United States Patent
Bookbinder et al.

(10) Patent No.: US 9,198,643 B2
(45) Date of Patent: Dec. 1, 2015

(54) SURGICAL INSTRUMENT

(71) Applicant: GYRUS MEDICAL LIMITED, Cardiff (GB)

(72) Inventors: Steven Jonathan Bookbinder, Manchester (GB); Adrian Ovidiu Persu, Bristol (GB); Richard John Keogh, Caerphilly (GB)

(73) Assignee: GYRUS MEDICAL LIMITED, CARDIFF (DE)

( * ) Notice: Subject to any disclaimer, the term of this patent is extended or adjusted under 35 U.S.C. 154(b) by 235 days.

(21) Appl. No.: 13/679,367

(22) Filed: Nov. 16, 2012

(65) Prior Publication Data
US 2013/0226155 A1    Aug. 29, 2013

(30) Foreign Application Priority Data
Nov. 16, 2011    (GB) .................................. 1119734.0

(51) Int. Cl.
| | |
|---|---|
| *A61B 17/00* | (2006.01) |
| *A61M 25/01* | (2006.01) |
| *A61B 17/29* | (2006.01) |
| *A61B 18/14* | (2006.01) |

(52) U.S. Cl.
CPC ............ *A61B 17/00* (2013.01); *A61M 25/0147* (2013.01); *A61B 18/1492* (2013.01); *A61B 2017/00323* (2013.01); *A61B 2017/2912* (2013.01); *A61M 25/0136* (2013.01)

(58) Field of Classification Search
CPC .......... A61B 1/00; A61B 17/00; A61B 18/04; A61B 18/492; A61M 25/00; A61M 25/0147
USPC ................ 600/146; 604/95, 525; 606/205, 32
See application file for complete search history.

(56) References Cited

U.S. PATENT DOCUMENTS

| | | | | |
|---|---|---|---|---|
| 4,996,974 | A | * | 3/1991 | Ciarlei .......................... 600/149 |
| 5,250,073 | A | * | 10/1993 | Cottone, Jr. ................... 606/206 |
| 5,273,535 | A | * | 12/1993 | Edwards et al. ........... 604/95.01 |

(Continued)

FOREIGN PATENT DOCUMENTS

WO    94/01162    1/1994

OTHER PUBLICATIONS

UK Search Report for Application No. GB1119734.0, dated Feb. 27, 2012.

(Continued)

*Primary Examiner* — William Thomson
*Assistant Examiner* — Victor Shapiro
(74) *Attorney, Agent, or Firm* — Nixon & Vanderhye P.C.

(57) ABSTRACT

A surgical instrument includes a housing, and a shaft including a proximal end, a deflectable portion and a distal tip. A handle is movable between first and second positions on the housing, and an actuator is movably coupled to the handle, such that movement of the handle between its first and second positions causes a corresponding movement of the actuator between first and second positions in the housing. A deflection wire includes proximal and distal portions, the distal portion being fixed to the shaft, and the proximal portion being affixed to the housing so as to provide a path length for the deflection wire within the housing. The movement of the handle causes the actuator to move to its second position, the second position of the actuator causing an increase in the path length for the deflection wire so as cause a deflection of the distal tip of the shaft.

11 Claims, 8 Drawing Sheets

(56) References Cited

U.S. PATENT DOCUMENTS

| | | |
|---|---|---|
| 5,624,397 A | 4/1997 | Snoke et al. |
| 5,683,412 A | 11/1997 | Scarfone |
| 5,976,075 A | 11/1999 | Beane et al. |
| 6,126,633 A | 10/2000 | Kaji et al. |
| 6,146,355 A * | 11/2000 | Biggs .......................... 604/95.01 |
| 6,283,960 B1 | 9/2001 | Ashley |
| 7,918,848 B2 * | 4/2011 | Lau et al. ........................ 606/29 |
| 2010/0217072 A1 | 8/2010 | Kondoh et al. |

OTHER PUBLICATIONS

Search Report issued in corresponding UK Application No. GB1219970.9, Date of Search: Jan. 30, 2013.

Search Report issued in corresponding EP Application No. 12191490.7-1659, Date of Search: Feb. 11, 2013.

* cited by examiner

SURGICAL INSTRUMENT

This application claims priority to UK Application No. 1119734.0, filed 16 Nov. 2011, the entire contents of which are hereby incorporated herein by reference.

This invention relates to a surgical instrument and in particular to an instrument in which the tip of the instrument can be articulated to assume various different angles or directions. There are a number of known articulated surgical instruments, and the most common method of effecting the articulation of the tip is to employ a deflection wire which, when pulled by the actuation of a handle or button, acts to cause the tip of the instrument to deflect. Examples are disclosed in U.S. Pat. Nos. 5,766,196, 5,857,964 and 6,645,218. Another example is in U.S. Pat. No. 6,283,960, in which a deflection wire is affixed directly to an actuator movably coupled to a handle. The present invention attempts to provide an improvement to these prior art instruments.

According to one aspect of the invention, there is provided a surgical instrument comprising a housing, a shaft including a proximal end, a deflectable portion and a distal tip, the proximal end of the shaft being coupled to the housing and the deflectable portion being movable between a straight position and a deflected position, a handle movable between a first position and a second position, an actuator movably coupled to the handle such that movement of the handle between its first and second positions causes a corresponding movement of the actuator between a first and a second actuator position, and a deflection wire including a proximal portion and a distal portion, the distal portion being fixed to the shaft, and the proximal portion being affixed to the housing so as to provide a path length for the deflection wire within the housing, the deflection wire having a first path length when the deflectable portion is in its straight position, the arrangement being such that a movement of the handle from its first position to its second position causes the actuator to move to its second position, the second position of the actuator causing an increase in the path length to a second path length, the second path length being longer than the first path length so as cause a deflection of the deflectable portion.

In this way the deflection wire is attached, not to the actuator, but to the housing, and the actuator acts to change the path length of the deflection wire. This allows greater control over the movement of the deflection wire, and also easier assembly of the surgical instrument. By the term "deflection wire", there is herein meant to include wires, cables and any elongate element capable of causing the deflection of the shaft, and of having sufficient flexibility that its path length within the housing is capable of being changed by the movement of the actuator. Obviously, the overall path length for the deflection wire is unchanged, as the deflection wire is not permanently deformed. However, the path length of the deflection wire within the housing is changed by the movement of the actuator, hence causing the corresponding path length of the deflection wire along the shaft to be correspondingly decreased. It is this change in path length along the shaft that causes the deflection of the shaft.

In a convenient arrangement, the actuator and the handle are integrally formed as a single component. Alternatively, the actuator and handle are conveniently formed as separate components, one with a cam and the other with a cam follower such that movement of the handle causes a corresponding movement of the actuator. Whether formed as one component or as separate components, movement of the handle causes a corresponding movement of the actuator, which acts on the deflection wire to change the path length between the distal end of the deflection wire and the point where it is attached to the housing. This change in the path length causes a corresponding deflection of the distal tip of the surgical instrument. This arrangement provides a surgical instrument which is easy to assemble, as the deflection wire can be installed within the housing before the actuator is added as a subsequent component.

According to one convenient arrangement, the deflection wire passes through a channel formed in the actuator. The actuator is conveniently adapted to pivot between its first position and its second position, the pivoting of the actuator changing the path length from the first path length to the second path length. The path length of the deflection wire is shorter when it passes through the channel when the actuator is in its first position, for example as the deflection wire passes through the actuator in a relatively straight line, aligned with the deflection wire on either side of the actuator. When the actuator is pivoted to its second position, the channel is realigned such that it is at an angle to the deflection wire on either side of the actuator. This causes the path length of the deflection wire to increase, thereby deflecting the tip of the surgical instrument. In one convenient arrangement, the actuator is adapted to pivot about a point towards its centre, but alternatively the actuator is conceivably adapted to pivot about a point towards one end thereof. Either way, the pivoting of the actuator increases the path length between the tip of the instrument and the point where the deflection wire is attached to the housing, thereby deflecting the instrument tip.

According to an alternative arrangement, the deflection wire passes over a movable spindle, the movement of the spindle changing the path length from the first path length to the second path length. In a first position, the spindle is relatively aligned with the path between the tip of the instrument and the point where the deflection wire is attached to the housing. Movement of the actuator causes the spindle to be moved such that it is laterally displaced from the aligned position, thereby increasing the path length and deflecting the tip of the instrument.

Conveniently, the spindle is fixed to the actuator such that movement of the actuator causes a corresponding movement of the spindle. Alternatively, the spindle is conceivably separate from the actuator, and the actuator includes a member adapted to contact the spindle and move it as the actuator moves from its first position to its second position. In this arrangement, the spindle is not a part of the actuator, but is moved by the member in response to movement of the actuator. Whichever way is employed, the movement of the actuator causes a corresponding movement of the spindle, thereby altering the path length of the deflection wire.

Conceivably, the movable spindle does not contact the deflection wire when the actuator is in its first position. According to a convenient arrangement, the deflection wire passes over a track formed in the housing when the actuator is in its first position, and is only contacted by the spindle as the actuator is moved from its first position to its second position. The spindle therefore only comes into play when the actuator is moved, and at all other times the deflection wire assumes its original position between the tip of the instrument and the point where it is attached to the housing. This provides a surgical instrument which is easy to assemble, as the deflection wire can be installed within the housing before the spindle is added.

This deflection arrangement can be utilised in a variety of different surgical instruments. For example, in one arrangement the instrument is an endoscope, capable of viewing a surgical site. Alternatively, the distal tip of the shaft conceivably carries an end effector. In this way the instrument can be a forceps, scissors or other type of surgical instrument capable of treating tissue at the surgical site. In a preferred arrangement, the instrument is an electrosurgical instrument.

According to another aspect of the invention, a surgical instrument comprises: a housing; an instrument shaft having a proximal end mounted to the housing and a distal tip spaced from the housing, the distal tip including a deflectable portion; a deflection wire which has a distal end coupled to the deflectable tip portion and a proximal end secured at a fixed location with respect to the housing and part of which, between the wire distal and proximal ends, lies within the housing, the coupling between the wire distal end and the deflectable tip portion being such that when the wire distal end moves relatively to the shaft the deflectable tip portion moves between an undeflected position and a deflected position; an actuator which is movably mounted to the housing and engages the said part of the wire lying within the housing such that movement of the actuator moves the wire to alter its path length within the housing so as to move the wire distal end and thereby to deflect the deflectable tip portion; and a handle for moving the actuator.

In any of the above described instruments, the actuator may be arranged to move the wire laterally in a region between a location at which it is confined within the shaft, and the said fixed location, the actuator engaging the wire wholly distally of the fixed location. Alternatively, the wire may be looped around a portion of the actuator and its proximal end is fixed in the housing at a location which lies distally of a portion of the wire loop lying furthest from the shaft.

The invention will now be further described, by way of example only, with reference to the accompanying drawings, in which.

Figure 1:
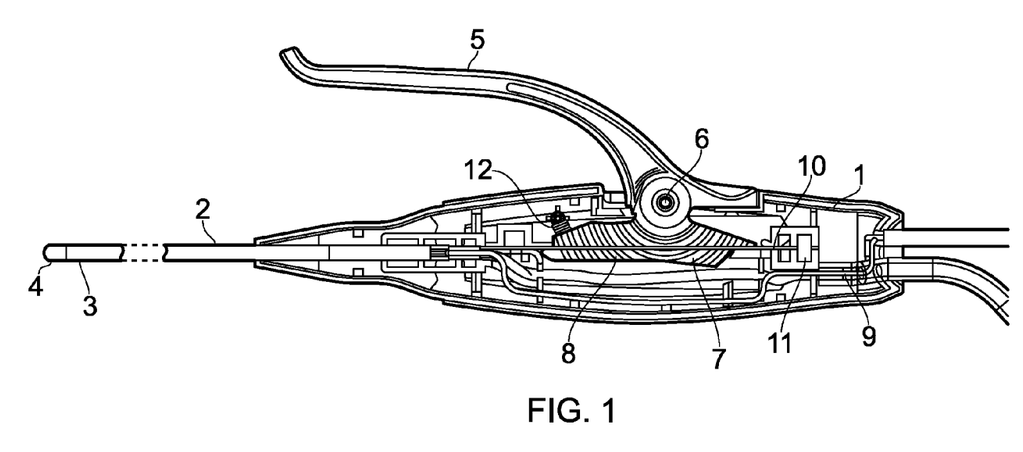
FIG. 1 is a schematic sectional view of a surgical instrument in accordance with the present invention, shown in an undeflected position.
Figure 2:
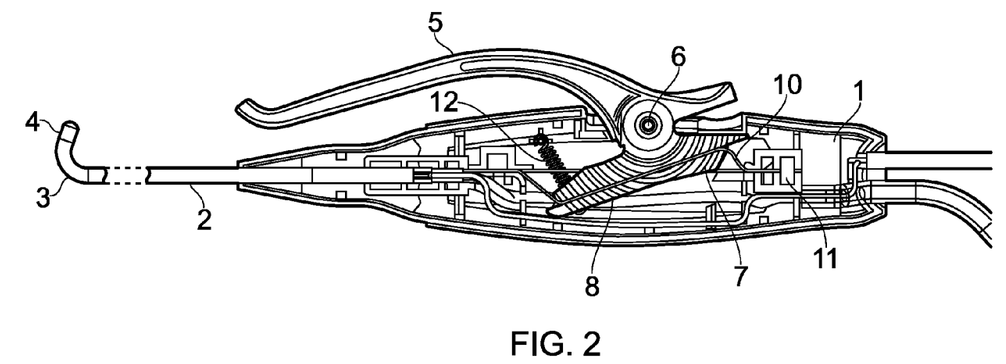
FIG. 2 is a schematic sectional view of the surgical instrument of FIG. 1, shown in a deflected position.

Referring to FIGS. 1 and 2, a surgical instrument comprises a housing 1 with a shaft 2 terminating in a distal tip 3 containing an end effector 4. In the instrument of FIG. 1, the end effector 4 is a bipolar electrosurgical electrode assembly capable of cutting or coagulating tissue. The housing 1 also contains a handle 5, pivotable about a pivot point 6. Attached to the handle (and integral thereto) is an actuator 7 in the form of an elongated block having a channel 8 running longitudinally therethrough. Also contained within the housing is an electrical lead 9 for the electrosurgical electrode assembly and a deflection wire 10. The deflection wire 10 is attached to the housing at an attachment point 11, and runs along the shaft 2 to terminate at the distal tip 3. The deflection wire 10 runs through the channel 8 in the actuator 7, before entering the shaft. A spring 12 biases the actuator 7 towards its "at rest" position, which is shown in FIG. 1 in which the channel is axially aligned with the deflection wire 10, and the distal tip 3 of the instrument is undeflected.

In order to deflect the distal tip 3 of the instrument, the user presses on the handle 5 to pivot it about the pivot point 6 and move it from the "at rest" position shown in FIG. 1 to the "deflected" position as shown in FIG. 2. This causes the actuator 7 to be moved to the position shown in FIG. 2 in which the channel is no longer axially aligned with the longitudinal axis running from the attachment point 11 to the shaft 2. This means that the deflection wire 10 is forced to assume an angled profile along part of its length, thereby increasing the path length of the deflection wire through the housing 1. As the deflection wire 10 is of a fixed finite length, this increase in the path length through the housing causes the deflection wire to pull on the distal tip 3 of the surgical instrument, resulting in a corresponding deflection of the distal tip into the deflected position shown in FIG. 2. In this way, the pivoting of the handle 5 causes a corresponding deflection of the distal tip 3, allowing the user to control the deflection of the tip at will.

Figure 3:
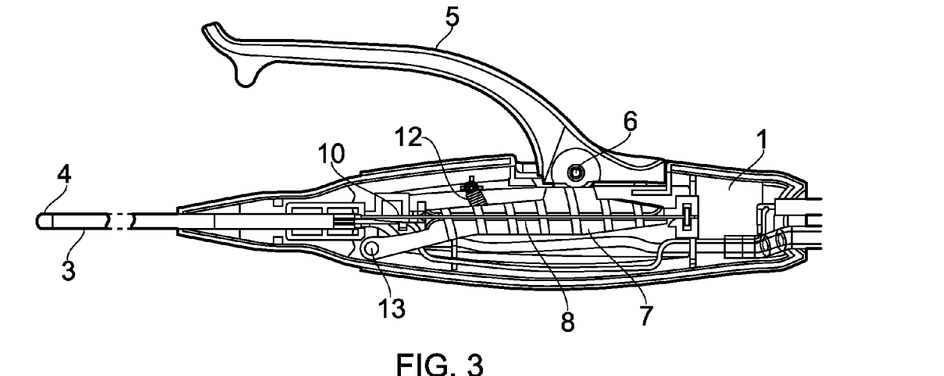
FIG. 3 is a schematic sectional view of a surgical instrument in accordance with an alternative embodiment of the present invention, shown in an undeflected position.
Figure 4:
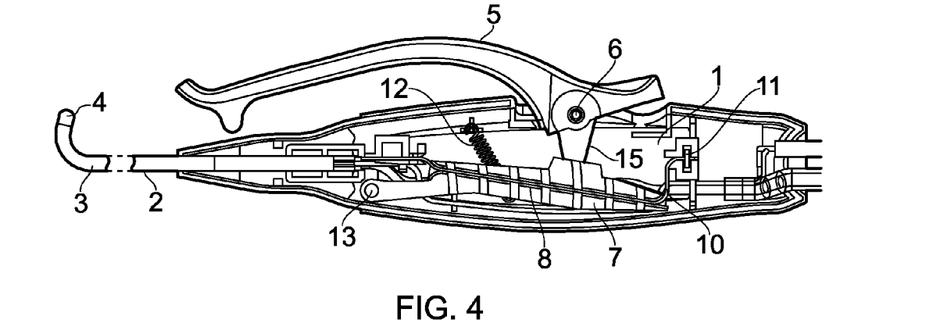
FIG. 4 is a schematic sectional view of the surgical instrument of FIG. 3, shown in a deflected position.
Figure 5:
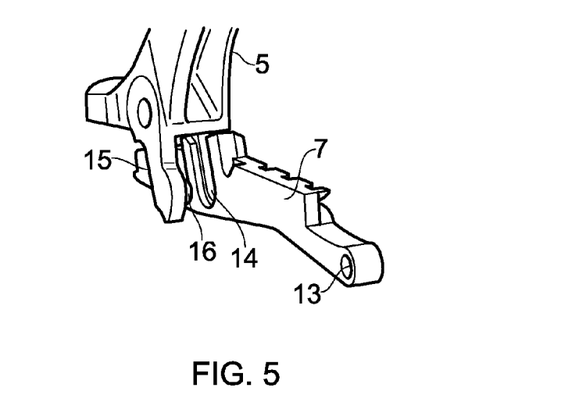
FIG. 5 is a schematic perspective view of a certain components of the surgical instrument of FIGS. 3 and 4.

FIGS. 3 to 5 show an alternative instrument, in which the housing 1, shaft 2 and handle 5 etc. are as previously described. Unlike in the instrument of FIGS. 1 and 2, the actuator 7 is not part of the handle 5, but is a separate component mounted via pivot point 13, the pivot point 13 being towards the distal end of the actuator. As shown most clearly in FIG. 5, the actuator includes a cam track 14, and the handle 5 includes a member 15 including a cam follower 16 such that a movement of the handle 5 causes the actuator 7 to pivot about the pivot point 13. As before, the actuator includes a channel 8 in which the deflection wire 10 is received.

Also as before, a spring 12 biases the actuator towards the position shown in FIG. 3, in which the channel is axially aligned with the deflection wire 10, and the distal tip 3 of the instrument is undeflected. To deflect the tip of the instrument, the user pivots the handle 5 about the pivot point 6, which causes the cam follower 16 to move in the cam track 14 to pivot the actuator 7 about pivot point 13. This pivoting of the actuator 7 results in the channel no longer being axially aligned with the longitudinal axis running from the attachment point 11 to the shaft 2. This means that the deflection wire 10 is once again forced to assume an angled profile along part of its length, thereby increasing the path length of the deflection wire through the housing 1, and causing a corresponding deflection of the distal tip 3 of the surgical instrument.

Figure 6:
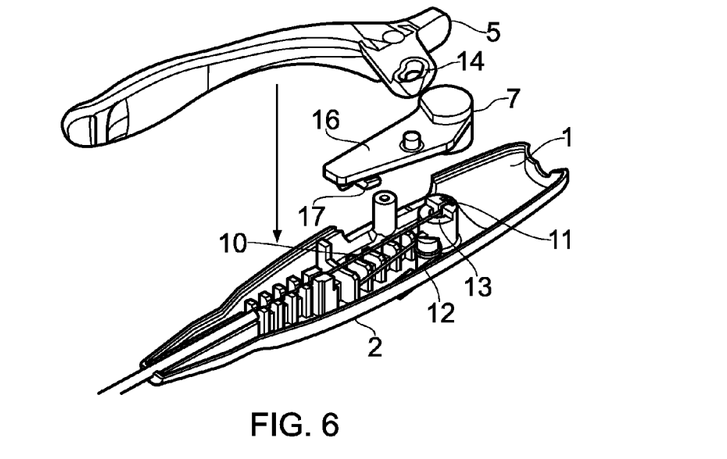
FIG. 6 is an exploded view of a surgical instrument in accordance with an alternative embodiment of the present invention.
Figure 7:
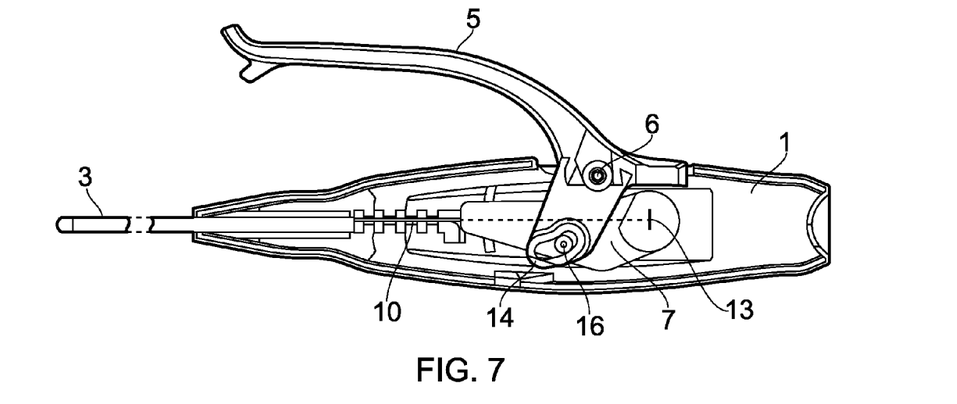
FIG. 7 is a schematic sectional view of the surgical instrument of FIG. 6, shown in an undeflected position.
Figure 8:
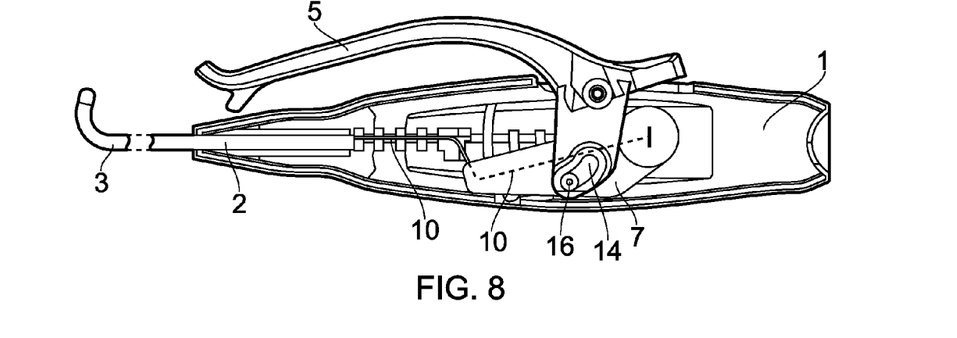
FIG. 8 is a schematic sectional view of the surgical instrument of FIG. 6, shown in a deflected position.

FIGS. 6 to 8 show an alternative instrument in which the cam track 14 is present on the handle 5 and the cam follower 16 is present on the actuator 7. The actuator is once again mounted via pivot point 13, the pivot point this time being at the proximal end of the actuator. As previously described, the actuator 7 is provided with a channel 8 in which the deflection wire 10 is received. As before, a pivoting of the handle 5 about pivot point 6 causes the cam follower 16 to move in the cam track 14 and pivot the actuator 7 about pivot point 13. As the actuator 7 pivots, the deflection wire 10 is deflected from its original path, as shown in FIG. 8. This deflection of the deflection wire 10 increases the path length of the deflection wire through the housing 1, causing a corresponding deflection of the distal tip 3 of the surgical instrument.

Figure 9:
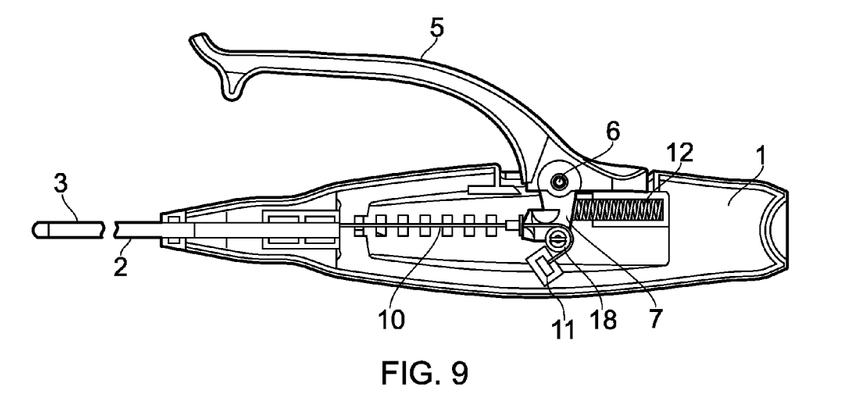
FIG. 9 is a schematic sectional view of a surgical instrument in accordance with a further alternative embodiment of the present invention, shown in an undeflected position.
Figure 10:
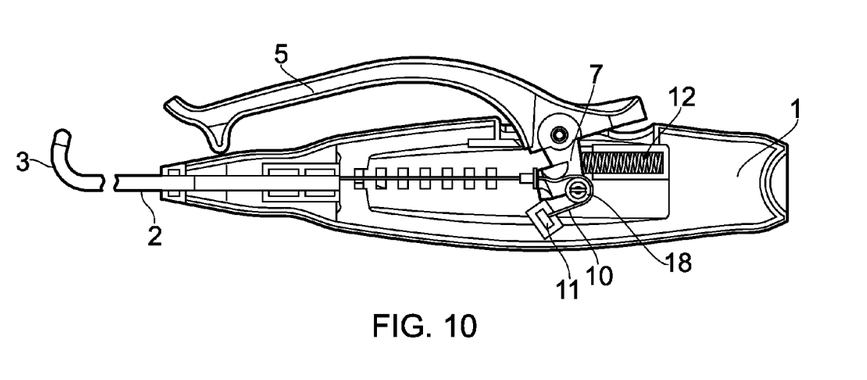
FIG. 10 is a schematic sectional view of the surgical instrument of FIG. 9, shown in a deflected position.

FIGS. 9 and 10 show an alternative instrument in which the deflection wire 10 is attached to the housing 1 at an attachment point 11 which is laterally offset from the longitudinal axis of the shaft 2, the deflection wire 10 running around a spindle 18 before reaching the attachment point 11. The spindle 18 is an integral part of the actuator 7, which is itself an integrally moulded component together with the handle 5. As before, compression spring 12 maintains the actuator 7 and hence the handle 5 in the "at rest" position shown in FIG. 9. When the user wishes to cause a deflection of the distal tip 3 of the surgical instrument, the user pivots the handle 5 about the pivot point 6 to the position shown in FIG. 10. In this position the pivoting of the handle 5 has caused the actuator 7 to move and hence moved the spindle 18 such that it is more proximally positioned as compared to its position in FIG. 9. This movement of the spindle creates an increased path length for the deflection wire 10 through the housing 1, causing a corresponding deflection of the distal tip of the instrument.

Figure 11:
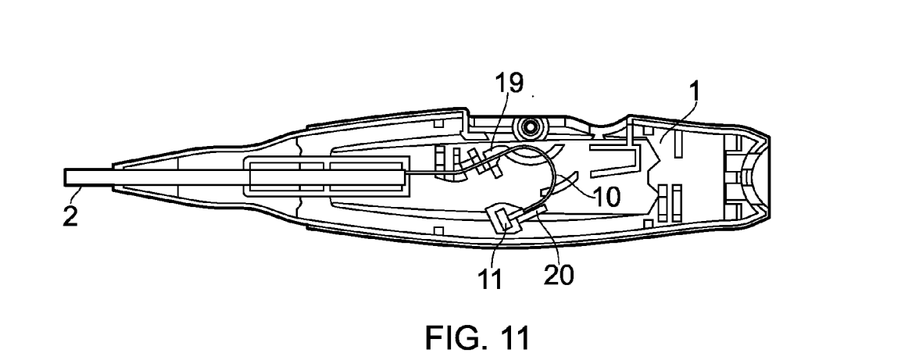
FIG. 11 is a schematic sectional view of the housing of a surgical instrument in accordance with a further alternative embodiment of the present invention, together with some other components.
Figure 12:
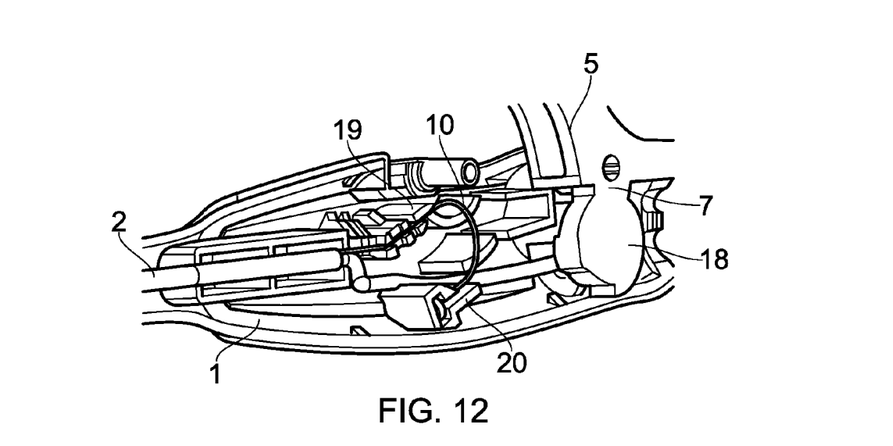
FIG. 12 is an exploded sectional perspective view of the surgical instrument of FIG. 11.
Figure 13:
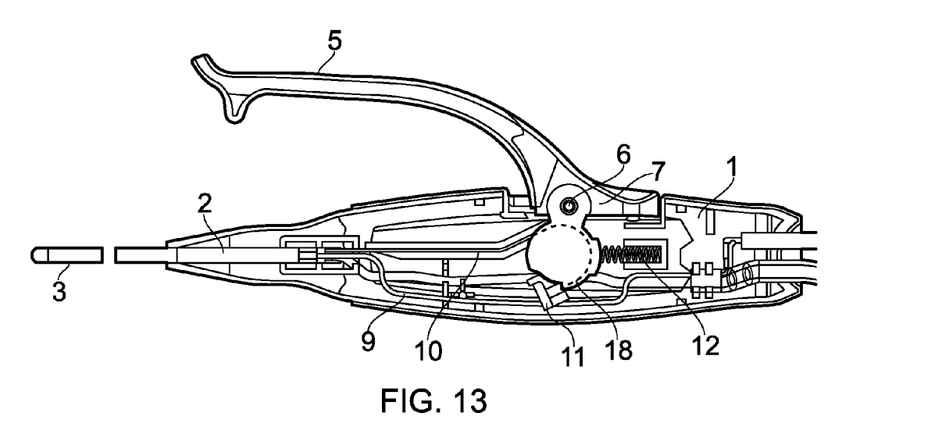
FIG. 13 is a schematic sectional view of the surgical instrument of FIG. 12, shown in an undeflected position.
Figure 14:
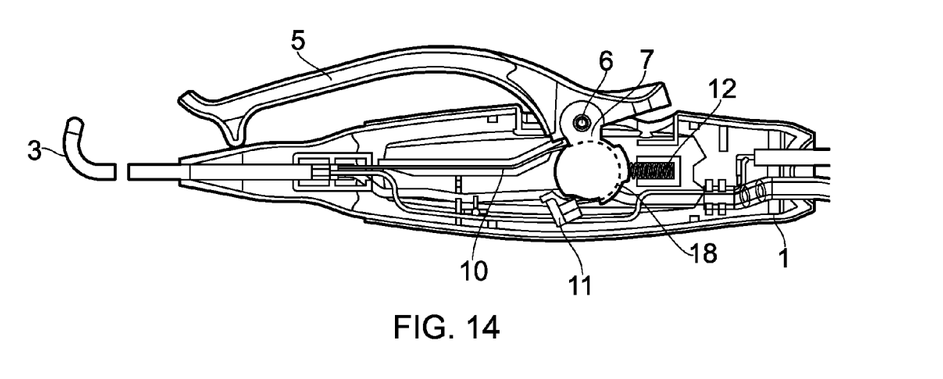
FIG. 14 is a schematic sectional view of the surgical instrument of FIG. 12, shown in a deflected position.
Figure 15:
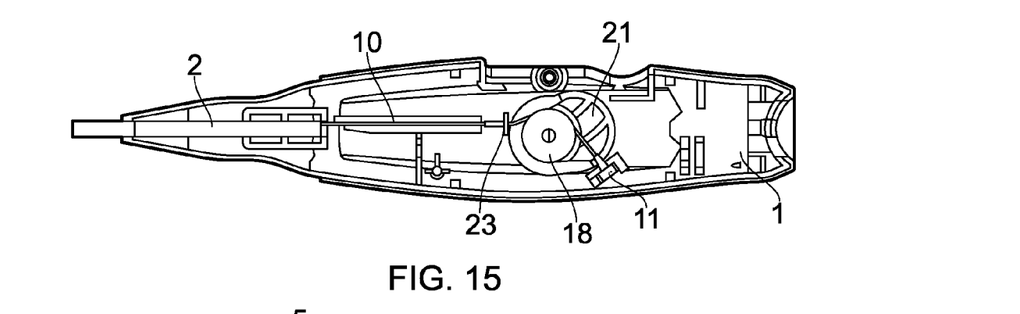
FIG. 15 is a schematic sectional view of the housing of a surgical instrument in accordance with a further alternative embodiment of the present invention, together with some other components.
Figure 16:
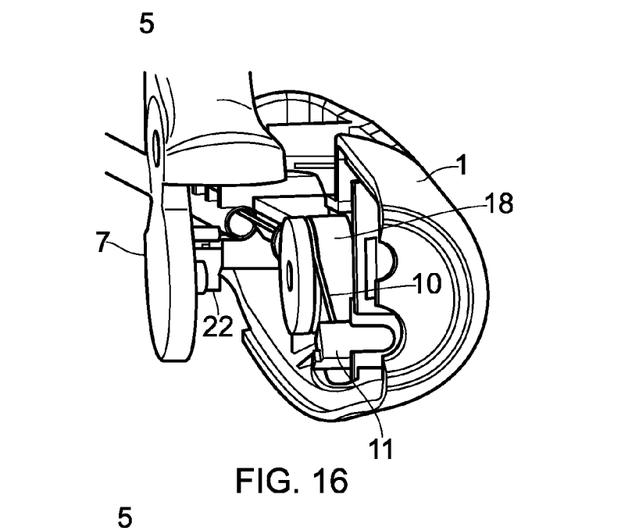
FIGS. 16 and 17 are exploded sectional perspective views of the surgical instrument of FIG. 15.
Figure 17:
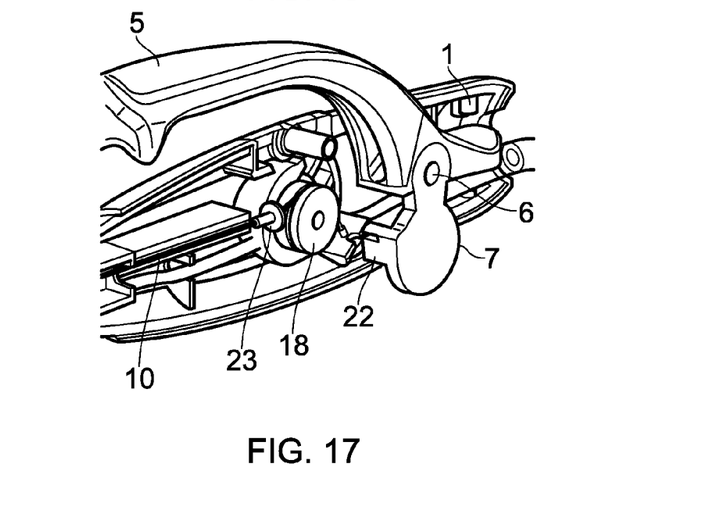
Figure 18:
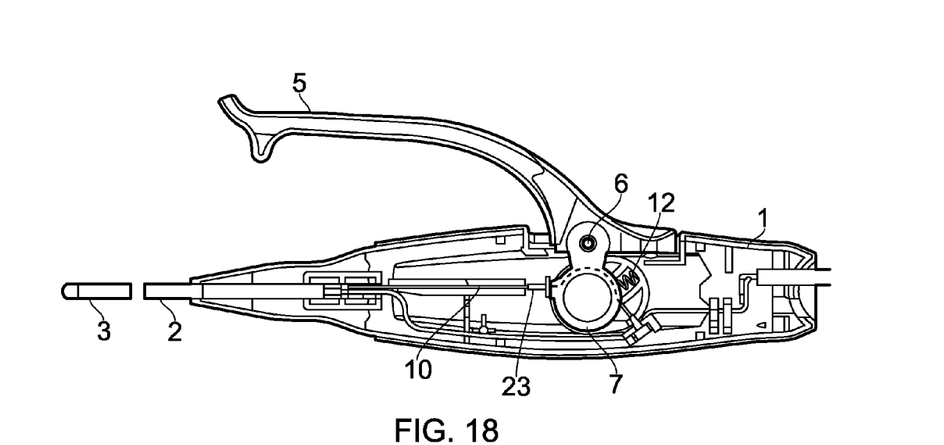
FIG. 18 is a schematic sectional view of the surgical instrument of FIGS. 16 and 17, shown in an undeflected position, and FIG. 19 a schematic sectional view of the surgical instrument of FIGS. 16 and 17, shown in a deflected position.
Figure 19:
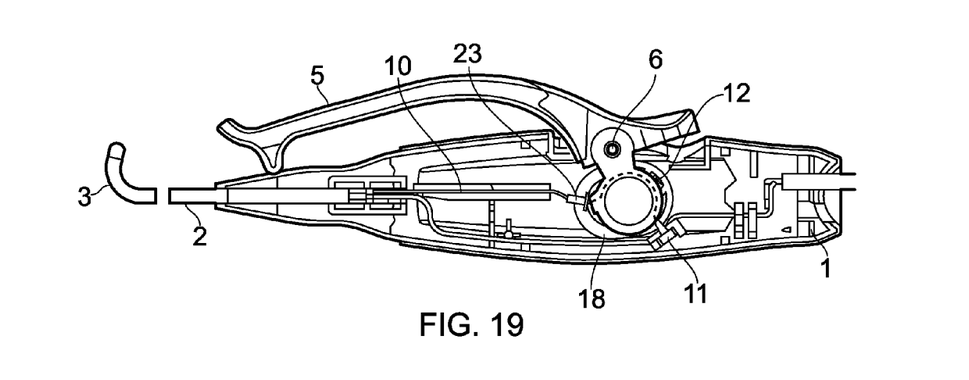

FIGS. 1 to 14 show an alternative instrument, in which the deflection wire 10 is not constrained by the spindle 18 when the handle 5 is in its "at rest" position, but is instead constrained by ribs 19, 20 present on the housing 1. The ribs 19, 20 cause the deflection wire 10 to assume a curved configuration, as shown in FIG. 11. The spindle 18 is attached to actuator 7 as before, and the pivoting of the handle 5 causes the spindle 18 to move proximally and pick up the deflection wire 10 from the ribs 19, 20. The further proximal movement of the spindle 18 as shown in FIG. 14 once again increases the path length for the deflection wire 10 through the housing, causing a corresponding deflection of the distal tip 3 of the instrument.

A final alternative instrument is shown in FIGS. 15 to 19, and includes a spindle as before, but this time the spindle 18 is located on the housing 1. The spindle 18 is located for movement along a track 21 and biased by spring 12 into the position shown in FIGS. 15 and 18. The deflection wire 10 runs over the spindle 18 before being attached to the housing at attachment point 11. The actuator 7 includes a spindle pick-up device 22, which engages the spindle 18 and moves it against the action of the spring 12 along the track 21. Pivoting of the handle 5 about pivot point 6, moves the actuator 7 and causes the pick-up device 22 to move the spindle 18 along the track into the position shown in FIG. 19. This once again increases the path length for the deflection wire 10 through the housing, causing a corresponding deflection of the distal tip 3 of the instrument. A crimp 23 present on the deflection wire 10 adjacent the pick-up device 22 allows the pick-up device to push the deflection wire back into its undeflected position when the handle is moved back to its original position, thereby returning the distal tip 3 of the instrument to its undeflected position.

It will be appreciated that alternative embodiments can be envisaged without departing from the inventive concept underlying the invention. Other actuator designs can be envisaged to increase the path length of the deflection wire, but a key factor is that the deflection wire is attached to the housing not to the actuator. The actuator only comes into play in order to increase the path length, not to secure the deflection wire within the housing. In this way, not only can a precisely controllable mechanism for deflecting the instrument be achieved, but the instrument can be assembled easily, with the deflection wire being positioned within the housing regardless of the presence or otherwise of the actuator.

What is claimed is:

1. A surgical instrument comprising:
   a housing;
   a shaft including a proximal end, a deflectable portion and a distal tip, the proximal end of the shaft being coupled to the housing and the deflectable portion being movable between a straight position and a deflected position,
   a handle movable between a first position and a second position,
   an actuator movably coupled to the handle such that movement of the handle between its first and second positions causes the actuator to pivot between a first actuator position and a second actuator position,
   a longitudinal channel extending through the actuator, the longitudinal channel including a proximal end and a distal end, and
   a deflection wire passing through the longitudinal channel in the actuator so as to pass the proximal end and the distal end of the longitudinal channel, the deflection wire including a proximal portion and a distal portion, the distal portion being fixed to the shaft, and the proximal portion being affixed to the housing so as to provide a path length for the deflection wire within the housing, the deflection wire having a first path length within the housing when the deflectable portion of the shaft is in its straight position, and a second path length within the housing when the deflectable portion of the shaft is in its deflected position,
   the arrangement being such that a movement of the handle from its first position to its second position causes the actuator to pivot from its first actuator position to its second actuator position, the second actuator position of the actuator reorienting the longitudinal channel from a first orientation to a second orientation so that the movement of the channel causes either the proximal end or the distal end of the channel to engage the deflection wire and thereby cause an increase in the deflection wire path length within the housing from the first path length to a second path length within the housing, the second path length being longer than the first path length so as cause a deflection of the deflectable portion of the shaft.

2. The surgical instrument according to claim 1, wherein the actuator and the handle are integrally formed as a single component.

3. The surgical instrument according to claim 1, wherein the actuator and handle are formed as separate components, one with a cam and the other with a cam follower such that movement of the handle causes a corresponding movement of the actuator.

4. The surgical instrument according to claim 1, wherein the actuator is adapted to pivot about a point towards its centre.

5. The surgical instrument according to claim 1, wherein the actuator is adapted to pivot about a point towards one end thereof.

6. The surgical instrument according to claim 1, wherein the instrument is an endoscope.

7. The surgical instrument according to claim 1, wherein the distal tip of the shaft carries an end effector.

8. The surgical instrument according to claim 7, wherein the instrument is an electrosurgical instrument.

9. A surgical instrument comprising;
- a housing;
- an instrument shaft having a proximal end mounted to the housing and a distal tip spaced from the housing, the distal tip including a deflectable portion;
- a deflection wire which has a distal end coupled to the deflectable tip portion and a proximal end secured at a fixed location with respect to the housing and part of which, between the wire distal and proximal ends, lies within the housing, the coupling between the wire distal end and the deflectable tip portion being such that when the wire distal end moves relatively to the shaft the deflectable tip portion moves between an undeflected position and a deflected position;
- an actuator which is movably mounted to the housing, and
- a longitudinal channel extending through the actuator, the longitudinal channel including a proximal end and a distal end,
- the deflection wire extending through the longitudinal channel so as to pass the proximal end and the distal end of the longitudinal channel, such that movement of the actuator and thus the longitudinal channel causes the channel to move and thereby either the proximal end or the distal end of the channel to engage the deflection wire and thereby cause the wire to alter and increase its path length within the housing so as to move the wire distal end and thereby to deflect the deflectable tip portion; and
- a handle for moving the actuator.

10. The instrument according to claim 9, wherein the actuator is arranged to move the wire laterally in a region between a location at which it is confined within the shaft and the said fixed location, the actuator engaging the wire wholly distally of the fixed location.

11. The instrument according to claim 9, wherein the proximal end of the wire is fixed in the housing.

* * * * *